United States Patent [19]

Lafortune et al.

[11] 4,278,093
[45] Jul. 14, 1981

[54] INTERCHANGEABLE PACEMAKER CONNECTOR FOR LEADS

[75] Inventors: Ray Lafortune, Chatsworth; Waldemar Heeb, Sepulveda, both of Calif.

[73] Assignee: American Technology, Inc., Northridge, Calif.

[21] Appl. No.: 785,928

[22] Filed: Apr. 8, 1977

Related U.S. Application Data

[63] Continuation-in-part of Ser. No. 693,943, Jun. 8, 1976, abandoned.

[51] Int. Cl.² ............................................. A61N 1/36
[52] U.S. Cl. ................................ 128/419 P; 339/267
[58] Field of Search ........................... 128/418, 419 P; 339/270 R, 267; 279/53

[56] References Cited

U.S. PATENT DOCUMENTS

| | | | |
|---|---|---|---|
| 2,176,071 | 10/1939 | Hall | 279/53 |
| 2,644,929 | 7/1953 | Kumpf | 339/267 |
| 3,183,476 | 5/1965 | Sacks et al. | 339/270 R |
| 3,549,159 | 12/1970 | Kroener | 279/53 |
| 3,649,367 | 3/1962 | Purdy | 128/419 P |
| 3,760,332 | 9/1973 | Berkovits et al. | 128/419 P |
| 3,824,556 | 7/1974 | Berkovits et al. | 128/419 P |
| 3,871,382 | 3/1975 | Mann | 128/419 P |

*Primary Examiner*—William E. Kamm

[57] ABSTRACT

A connection in a cardiac pacemaker features a double ended fixed sleeve anchored midway between opposite sides of a pacemaker jacket in electric communication with the interior mechanism. The fixed sleeve is double ended and capable of accepting either of two collets of the same outside diameter at either end. One of the collets has a larger inside diameter than the other for connection to an electric lead wire of size corresponding to the respective inside diameter. An equalizer sleeve carrying a collet draw screw fits either end of the fixed sleeve and is mounted at the end opposite the selected collet. When occasion arises for reversing the lead connection, end for end, to connect, for example, a lead of different size, the first lead is released from the collet as is also the equalizer sleeve. The equalizer sleeve is then removed and located at the opposite end of the fixed sleeve and another collet having a different inside diameter for a different electric lead is inserted into the sleeve at the end opposite the new location of the equalizer sleeve, ready for attachment of the different electric lead.

Another form of the invention has a double ended collet, one end with a larger diameter opening then the other. There is a bushing at each end with a central passage screw threaded into the terminal shroud, each bushing having a hex wrench pocket so that a terminal can be inserted from either end and the collet tightened on it by wrench action at the opposite end.

13 Claims, 16 Drawing Figures

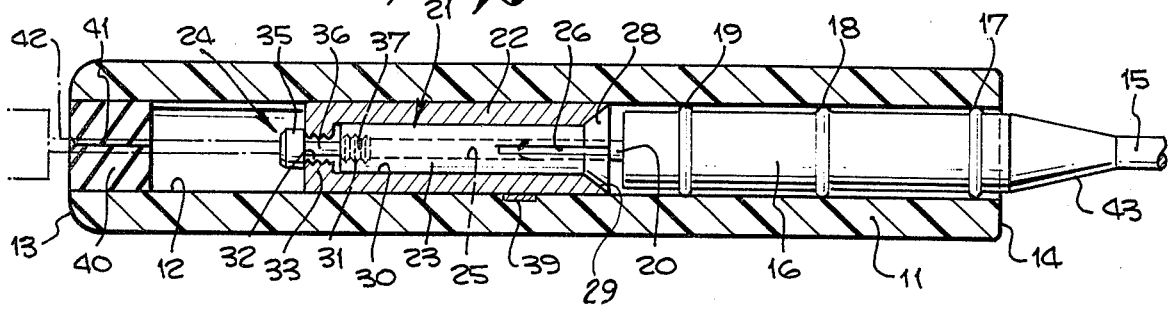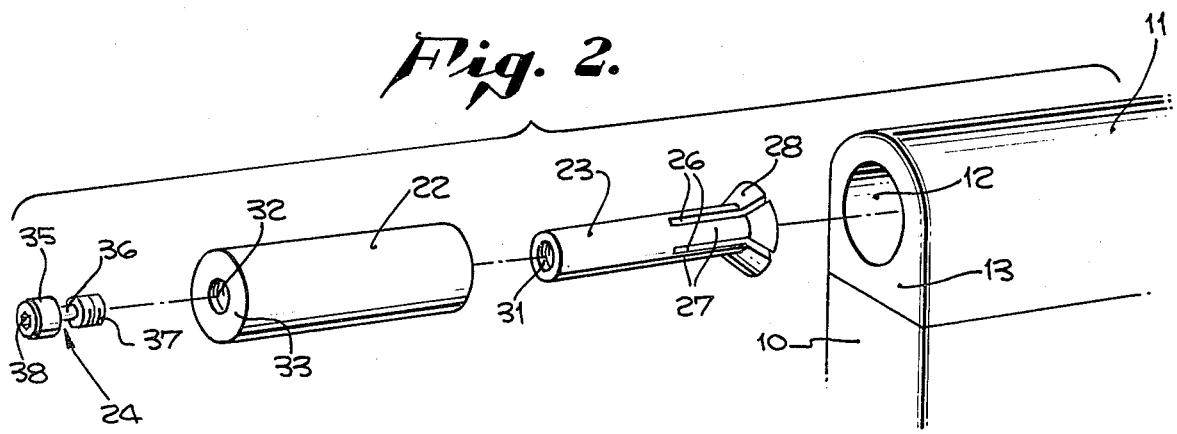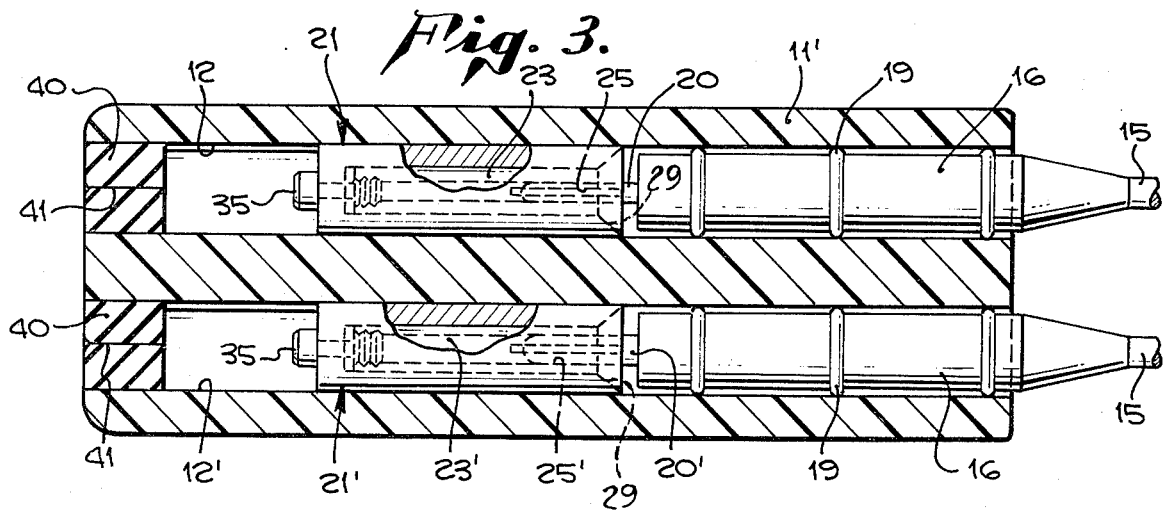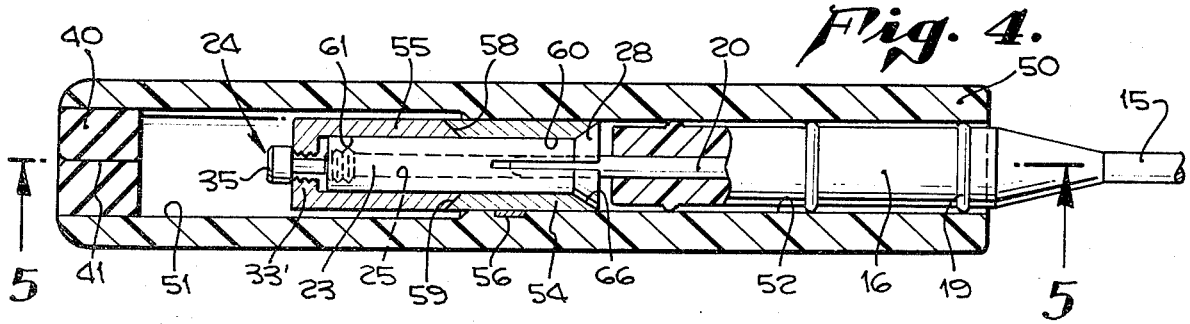

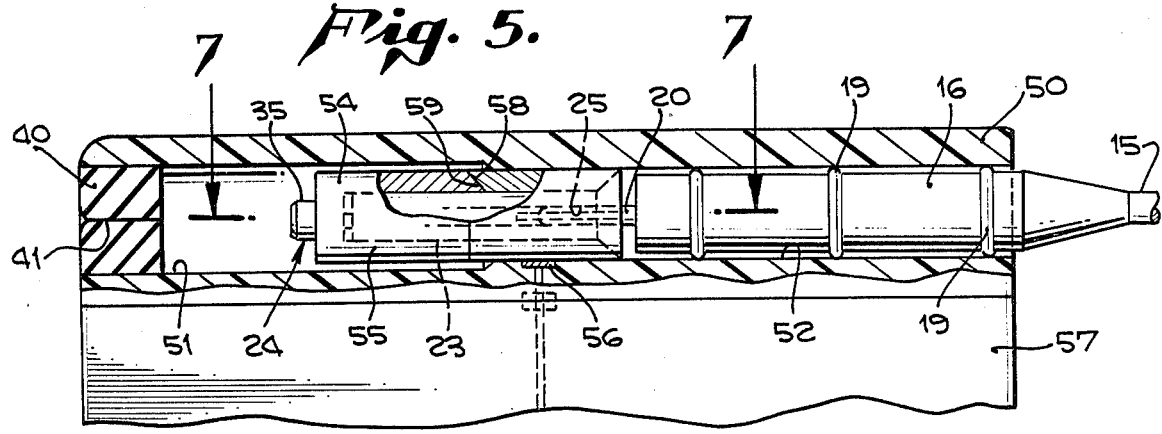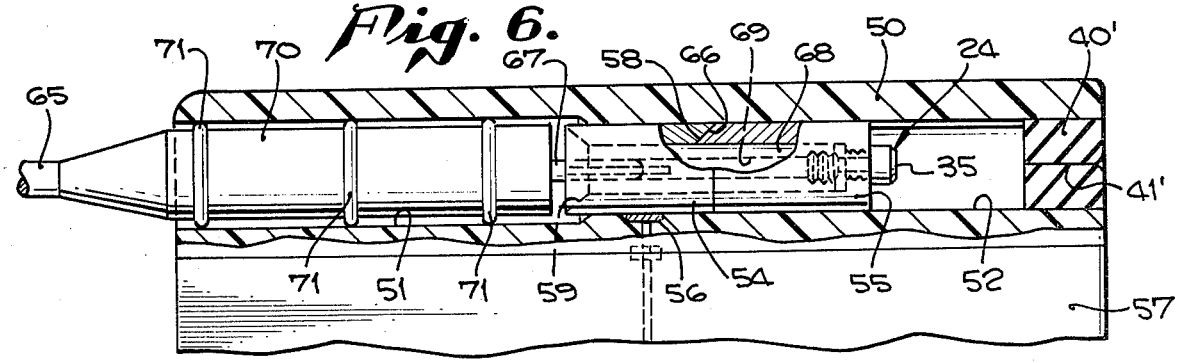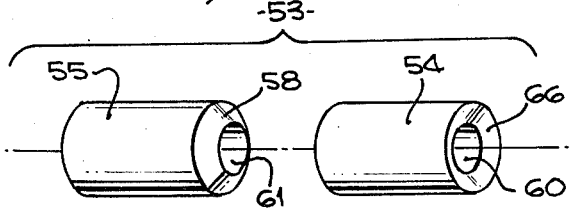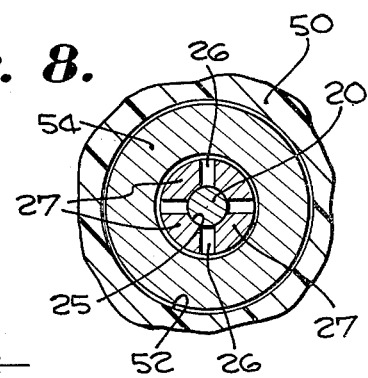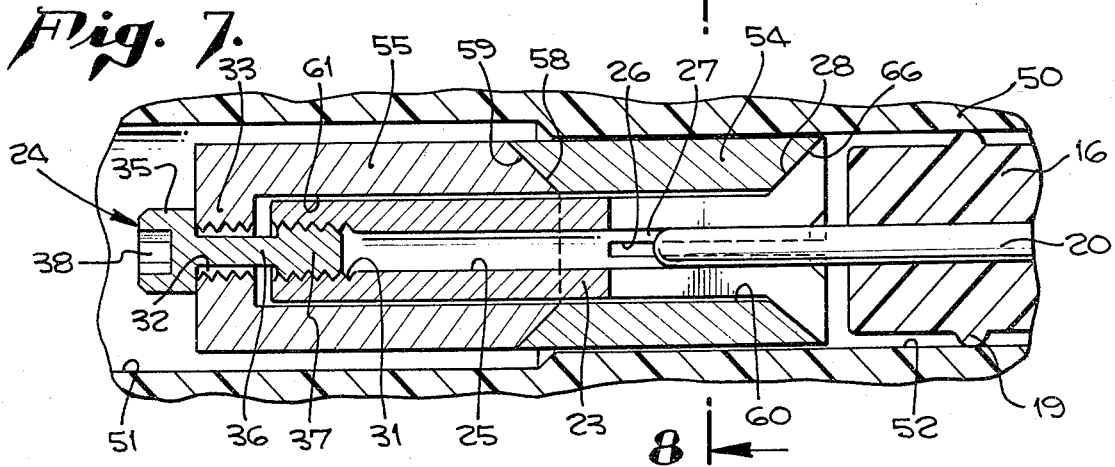

INTERCHANGEABLE PACEMAKER CONNECTOR FOR LEADS

This is a continuation-in-part of copending application Ser. No. 693,943, filed June 8, 1976, now abandoned.

Because cardiac pacemakers are implanted in the body, and must remain there for a long period of years, electric leads which direct current to the heart and which are connected to the pacemaker unit need to be connected with great assurance and at the same time be connected in such a way that body fluids are inhibited from contact with the leads whereby electrolysis could be set up at the connection and cause the connection to deteriorate. Occasions do arise, however, when the pacemaker must be removed and replaced as a complete unit, without need for disturbing the location of the leads which run intravenously to the heart. Consequently, the lead connections must be such that they remain with the unit but can be readily disconnected from the leads for removal of one pacemaker and replacement with another. Clearly, such connections must be positive, dependable, and capable of being quickly made and unmade.

A common expedient heretofore employed has been to fasten the lead in the connection by use of a set screw, after which the opening giving access to the set screw must be closed. A very troublesome difficulty with the set screw technique is inability on the part of the operator to be certain just how firmly to force the set screw into engagement with the lead. If the screw has been turned in too far, very commonly the lead is deformed in the socket provided for it. Thereafter when the set screw is loosened to remove the lead, the lead very commonly sticks in the recess and cannot be removed. Another difficulty with the set screw technique resides in the fact that the set screw needs to be pointed to be certain of making its way into the lead for a good connection, and it is most difficult for the surgeon implanting the pacemaker to be certain not to drive the set screw too far into the lead. Further still, there is no way by visual inspection for the surgeon to know whether or not the lead has been pushed far enough into the contact receptacle to be engaged by the set screw without making some exceptionally difficult physical tests after the connection has supposedly been made. Because of the point-like connection, usually between unlike metals, there has been a strong tendency for electrolysis to develop in the presence of body fluids which may seep into the connection.

It is therefore one of the objects of the invention to provide new and improved lead connections embodied in a pacemaker unit making the unit complete in itself, the lead connections being such as to assure a positive grip on the lead over a substantially large area of engagement and which when ready for disengagement can be positively released.

Another object of the invention is to provide a new and improved interchangeable cardiac pacemaker connection which can be quickly, easily, and positively made in a secure manner, and without likelihood of damage to the connection.

Still another object of the invention is to provide a new and improved interchangeable cardiac pacemaker lead connection which is of such character that by simple interchange of one element the connection can be made to accommodate leads of any one of a number of different sizes and kinds.

Still another object of the invention is to provide a new and improved interchangeable cardiac lead connection of such character that the lead can be brought in from either of two different directions, and under circumstances where the connection may be adjusted to accommodate leads of different sizes in the different directions, while at the same time assuring a quick, durable, positive connection which can be released at will.

Further included among the objects of the invention is to provide a new and improved interchangeable cardiac pacemaker lead connection which is small and compact, making possible employment with pacemakers of greatly reduced size, and which at the same time is capable of an extremely positive but at the same time releasable connection, capable of dependable performance over long periods of time.

With these and other objects in view, the invention consists of the construction, arrangement, and combination of the various parts of the device, whereby the objects contemplated are attained, as hereinafter set forth, pointed out in the appended claims and illustrated in the accompanying drawings.

FIG. 1 is a longitudinal sectional view of the pacemaker lead connection featuring a unidirectional collet.

FIG. 2 is an exploded perspective view of the operating parts of the connection of FIG. 1.

FIG. 3 is a longitudinal sectional view showing a part of unidirectional lead connections in a single housing.

FIG. 4 is a longitudinal sectional view of a bidirectional collet showing a lead connection on one side only.

FIG. 5 is a longitudinal sectional view on the line 5—5 of FIG. 4.

FIG. 6 is a longitudinal sectional view similar to FIG. 5 but showing the collet rearranged to accept a lead of different size from the opposite direction.

FIG. 7 is a fragmentary longitudinal enlarged sectional view on the line 7—7 of FIG. 5.

FIG. 8 is a cross-sectional view on the line 8—8 of FIG. 7.

FIG. 9 is an exploded perspective view of the two part sleeve used in the construction of the device of FIGS. 6, 7, and 8.

Figure 10:
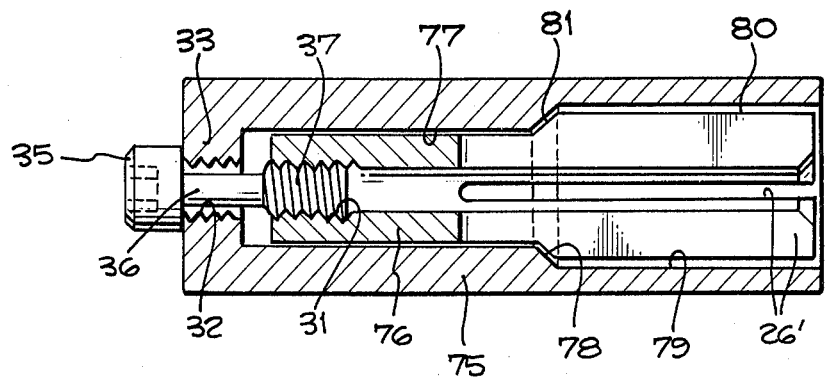
FIG. 10 is a longitudinal sectional view of a second form of sleeve and collet.

In an embodiment of the invention chosen for the purpose of illustration, the invention is housed in the unidirectional form of the device shown in FIGS. 1, 2, and 3. The pacemaker itself is represented by no more than a fragment of housing 10 which contains appropriate electronics, not shown, and at one end of which is provided a thermal shroud 11 of an appropriate epoxy or Silastic material. A bore 12 of uniform diameter throughout extends from one end 13 of the shroud to the other end 14, the bore being initially open at both ends. A single lead 15 is provided with a substantially standard type bushing 16 slightly smaller in outside diemater than the bore 12 and provided with integral resilient sealing beads 17, 18, and 19. An electrode 20 is sealed insulatively within the bushing 16 and lead 15, and is the element to which connection is to be made by the expedient of the disclosure.

The connection for receiving and being connected to the electrode 20 consists of a connector assembly indicated generally by the reference character 21. The connector consists of a sleeve 22, a collet 23, and a captive fastening screw 24. The collet 23 is somewhat conventional in its general appearance in that it includes a recess or pocket 25 in the shank for reception of the electrode 20, the recess being made of variable inside diameter at the right-hand end as shown in FIGS. 1 and 2 by reason of longitudinal slots 26 which divide the sleeve into segments 27. A generally truncated conical flared end 28 is adapted to be received in a countersink 29 at the end of a pocket 30 in the sleeve 22.

At the left end of the collet the recess 25 is provided with threads 31. These threads are identical in size and pitch to threads 32 in an end wall 33 of the sleeve 22. The captive fastening screw 24 serving as a draw screw has a head 35, a shaft 36, and a threaded boss 37, the head being provided with a hexagonal wrench pocket 38. The external threads of the threaded boss 37 are complementary to and adapted to engage with the internal threads 32 of the sleeve 22 and internal threads 31 of the collet 23. It is significant that the length of the shaft 36 is slightly greater than the thickness of the end wall 33, the relationship being shown in FIG. 1.

When the connector assembly 21 is mounted in the bore 12, as shown in FIG. 1, and a contact 39 is made with the electronics within the housing 10, the sleve is then effectively anchored in position. A plug 40 of appropriate resilient material is then anchored in one end, namely the left end as shown in FIG. 1, to effectively close that end of the bore 12. Extending through the plug is a slit 41 which provides access to the interior of the bore 12 for a hexagonal wrench 42, but wherein the plug is of such resilient material that once the wrench 42 has been withdrawn, the slit will be effectively closed against the passage of body fluids.

When the connecting assembly 21 is installed in the manner shown, the captive fastening screw 24 is already in place. This means that the threaded boss 37 has been threaded through the end wall 33 and overlies the inside face of the end wall inasmuch as the length of the shaft 36 is greater than the thickness of the end wall. When the connection is to be made, the bushing 16 is pushed into the bore 12 until the electrode 20 is projected for substantially its entire length into the recess 25 of the collet 23. So that the collet will be fully receptive, the head 35 of the fastening screw is rotated so as to extend the collet outwardly of the sleeve 22 to a position where the segments 27 are fully spread. After the electrode has been projected into the recess 25, the fastening screw 24 is rotated in a contrary direction by employment of the wrench 42 whereby to draw the collet in a direction right to left as viewed in FIG. 1 by the threaded engagement of the threaded boss 37 with the threads 31 of the collet. As the collet is drawn inwardly, the wall of the countersink 29 presses against the conical flared end 28 of the collet causing the segments 27 to be forced laterally against the electrode 20 and make the connection. Whether or not the electrode 20 has been pushed far enough in can be checked by inspecting the exterior end of the bushing 16 which will reveal the bushing entirely contained within the recess with only a sloping portions 43 exposed. Under such circumstances it is certain that when the collet has been tightened to engaged position, there will be an effective mechanical and electrical connection between the electrode and connection 39 through the connector assembly 21.

When, for any reason, the lead 15 is to be disconnected, it is necessary only to again project the wrench 42 through the plug 40 into the hexagonal wrench pocket 38 of the head 35 and back off the collet to release its engagement with the electrode 20.

Should there be an occasion where a lead 15 might be provided with an electrode 20 of diameter either greater or smaller than that adapted to be received within the collet 23, the collet can be released for replacement by another collet constructed in the same general fashion but with a recess 25' of different diameter, either larger or smaller, depending upon the size of the electrode which is to be accommodated. To release the collet the fastening screw 24 is rotated in an unthreading direction while pressure is applied against the right end of the collet, as viewed in FIG. 1. When the threaded engagement of the boss 37 is released with respect to the threads 31 of the collet, the collet can be knocked out of its position in the sleeve and withdrawn through the right end of the bore 12, after which a new collet can be inserted and engaged with the threads of the boss 37 to be ready for operation.

The versatility of the unidirectional assembly of FIGS. 1 and 2 is illustrated in FIG. 3 where a terminal shroud 11' is provided with two bores 12 and 12' which may be of the same diameter. The connector assemblies 21 and 21' are the same except for the provision of a collet 23' in the connector assembly 21' which has a recess 25' slightly larger than the recess 25 of the collet 23 to accommodate an electrode 20' which is larger in diameter than the electrode 20.

A bidirectional arrangement is shown in FIGS. 4 through 9, inclusive. For this arrangement a terminal shroud 50 is provided with a bore 51 of relatively larger diameter on the left side, as viewed in FIG. 4, and an interconnecting bore 52 on the right side of relatively smaller diameter. For this assembly, there is provided a two part sleeve indicated generally by the reference character 53 in FIG. 9, the sleeve comprising a fixed sleeve 54 and an equalizer sleeve 55.

The fixed sleeve is adapted to be anchored in position as shown in FIGS. 5 and 6 within the bore 52 and there interconnected by means of an electrical contact 56 with the electronics (not shown) within a housing 57.

As shown in FIGS. 4 and 5, the lead 15 and bushing 16 are projected into the bore 52 from the right side of the shroud 50. To accommodate this direction of application the equalizer sleeve is mounted at the left end of the fixed sleeve with a frusto-conical flared portion 58 received in a countersink 59. The collet 23 is secured in the pocket 60 of the fixed sleeve 54 and pocket 61 of the equalizer sleeve 55 by means of the captive fastening screw 24, in the same manner as has been described in connection with FIGS. 1 and 2. The recess 25 in the collet is of a size adapted to receive the electrode 20 of the lead 15, there to be tightened in place by manipulation of the captive fastening screw 24 as heretofore described by manipulation of an appropriate wrench projected through the slit 41 of the plug 40.

When a connection is to be made to a lead 65 at the opposite end of the terminal shroud 50, the parts need to be reversed end for end within the shroud, the fixed sleeve 54 however remaining in anchored position. The captive fastening screw 24 is rotated in an unthreading direction to first release the collet 23 which can be removed endwise from the right end of the bore 52, as shown in FIGS. 4 and 5. The plug 40 is removed and the equalizer sleeve 55 in company with the captive fastening screw 24 is then removed from the left end of the bore 51, and reapplied through the bore 52 to the right-hand end of the fixed sleeve 54, as shown in FIG. 6. In this position the frusto-conical flared portion 58 of the equalizer sleeve 55 fits into a countersink 66.

Because an electrode 67 may be of different size, a new collet 68 is provided which has in it a recess 69 of a size to accommodate the electrode 67. The new collet 68 externally is the same shape and size as the collet 25 and provided with the same segments and slots. The bore 51 is made larger to accommodate a bushing 70 for the lead 65 which may likewise be larger, and provided with the customary sealing beads 71. For this arrangement, the wrench 42 previously described is projected through a slit 41' in a plug 40' at the right-hand end of the bore 52 whereby to manipulate the captive fastening screw 24 in the same manner as has been previously described.

In the bidirectional arrangement the sizes of the respective bores 51 or 52 can be made as desired to accommodate whatever the size may be of the bushings for the respective leads. Although bores of different sizes have been shown, bores of the same sizes might be preferred on some occasions. Furthermore, because the fastening screw remains captive in the equalizer sleeve 55 making of these two parts a subassembly, the captive screw need never become misplaced even when the collet is released. Accordingly, the parts can be relatively simple while providing the versatility needed. The lateral squeezing of the segments of the collet provides a secure, electrically complete and dependable connection which irrespective of how tightly the connection may be made will produce no deformity in the electrode. Accordingly, when the collet is released, there will be no binding of the electrode in the collet and it can be readily withdrawn.

In the form of invention of FIG. 10 a sleeve 75 is provided with a collet 76, there being a recess 77 in the sleeve for reception of the collet. In this form of device a flared portion 78 in the recess accounts for an enlargement 79 of the recess near its open end. Correspondingly the collet 76 has an enlarged portion 80 complementary with respect to the enlargement 79. A flared portion 81 of the collet is substantially complementary to the flared portion 78 of the sleeve for the same purpose as has previously been described in connection with what had been designated as frusto-conical elements. It should be appreciated that the flared portions can assume a variety of configurations, frusto-conical structures merely being employed as representative means. In this form of the invention in FIG. 10 it is further significant that the complementary flared portions can be located intermediate opposite ends of the recess and not necessarily at the open end. In other respects the form of invention of FIG. 10, provided as it is with slots 26' is substantially the same as has been described in connection with FIG. 1 and figures related to FIG. 1.

Figure 11:
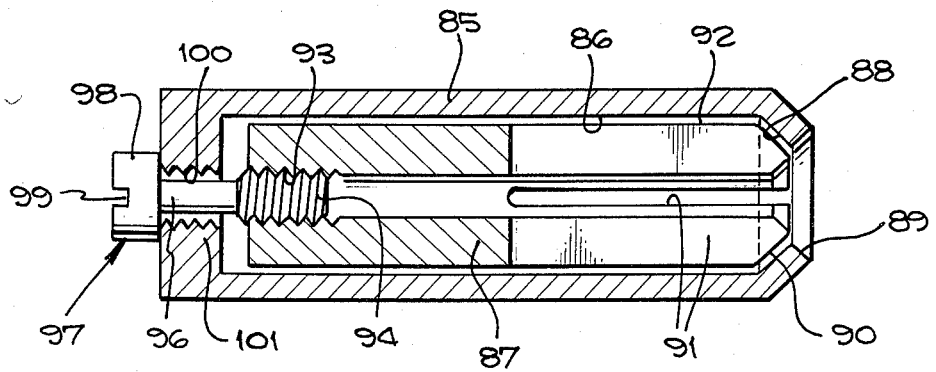
FIG. 11 is a longitudinal sectional view of a third form of sleeve and collet.

In the form of invention of FIG. 11 a sleeve 85 has a recess 86 substantially cylindrical throughout its length and accommodates a collet 87. In this instance there is an inwardly directed flared portion 88 inwardly of an opening 89 for the sleeve. The collet 87 has a complementarily flared portion 90 positioned within the open end 89. Slots 91 provide for contraction and expansion of adjacent fingers 92. Two, three, four or more slots and corresponding fingers may be provided in this and in other forms of the device. Additionally in this form of the device there is a reverse threaded opening 93 in an end wall 94, the threading of which is complementary to exterior threads 95 at the end of a shaft 96 of an appropriate captive fastening screw 97. A head 98 is provided with a customary tool slot 99. Reverse threads 100 in an end wall 101 of the sleeve freely surround the shank 96 and provide for threaded engagement with the exterior threads 95 when the captive fastening screw is initially inserted into the sleeve.

By reason of having reversely directed threads when the fastening screw is rotated in the customary direction which it would have for tightening the collet about an appropriate electric lead, the collet is pushed outwardly in a direction from left to right as viewed in FIG. 11 so that the complementary flared portions engage and press the fingers 92 inwardly to grip the lead. Reverse rotation of the fastening screw withdraws the collet inwardly in a direction from right to left thereby to release the fingers and a lead which has been previously attached.

Figure 12:
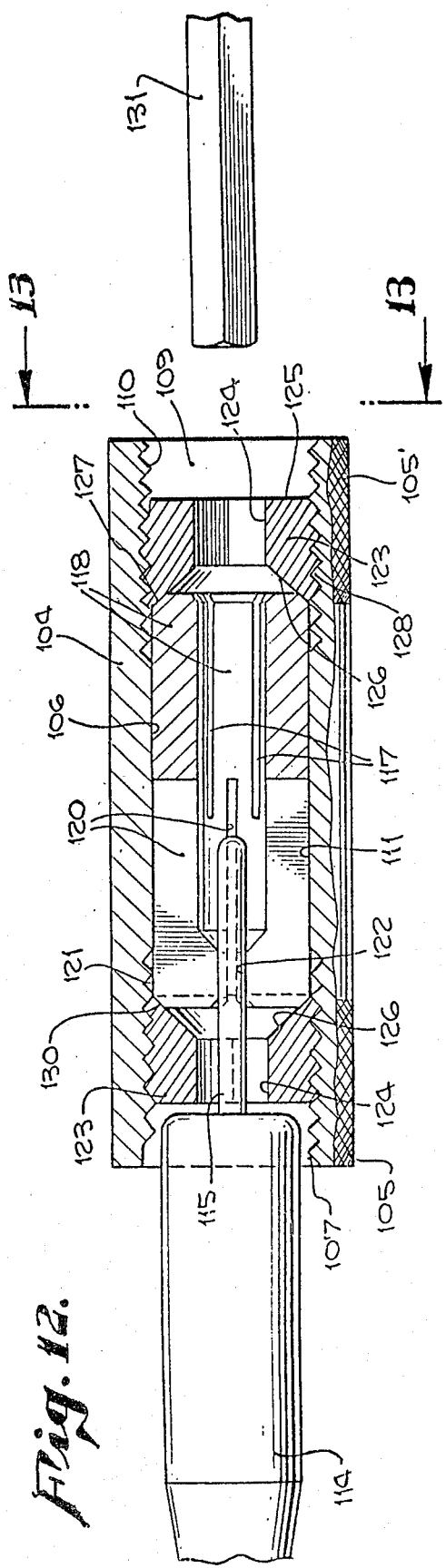
FIG. 12 is a longitudinal sectional view of another form of the invention assembled with a lead.

In a compact and simplified form of the invention shown in FIG. 12, there is provided a housing 104 of non-megnetic material, substantially cylindrical in its exterior form and provided with knurled exteriors 105, 105' at opposite ends. Through the housing 104 extends an axial passageway 106 having a port 107 at one end provided with an internal thread 108 and a port 109 at the opposite end provided with an internal thread 110. A mid portion 111 of the axial passage intermediate the threads 108 and 110 is smooth walled and cylindrical.

Adapted to be located within the axial passage 106 is a collett 113 of smooth walled cylindrical exterior form, the collett being adapted for reception of one lead or another to a pacemaker (not shown) which is adapted to contain the housing 104 and related parts. By way of example in FIG. 12 there is shown a lead 114 of conventional construction from which extends the customary wire core 115 which is adapted for insertion in the appropriate end of the collett 113. As previously described, leads like the lead 114 may have wire cores of slightly different size and the connector of FIG. 12 and related figures is designed to be one capable of accommodating a lead having a wire core of one diameter at one end or a lead having a wire core of a different diameter at the other end. Although this arrangement is particularly advantageous the construction is such that it could be built to accommodate a lead having the same wire core diameter at both ends.

Figure 14:
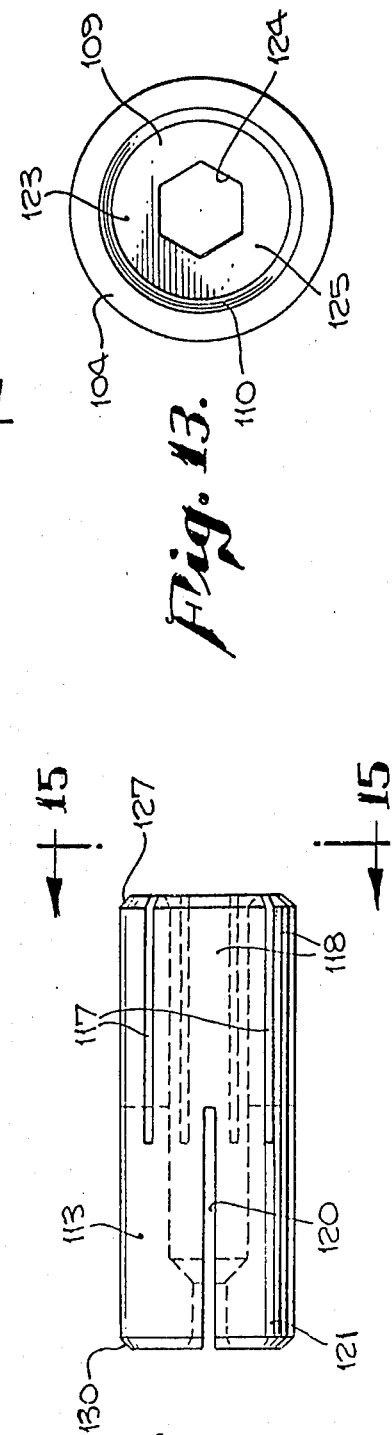
FIG. 14 is a side elevational view of the collet used in FIG. 12.
Figure 13:
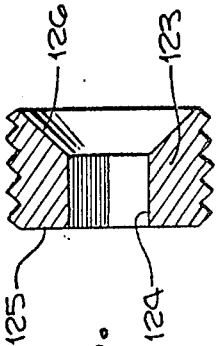
FIG. 13 is an end view on the line 13—13 of FIG. 12.
Figure 15:
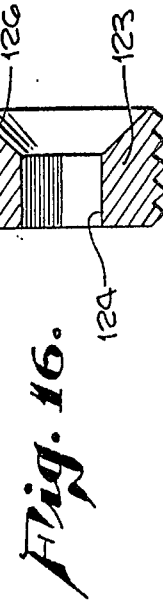
FIG. 15 is an end view on the line 15—15 of FIG. 14.
Figure 16:
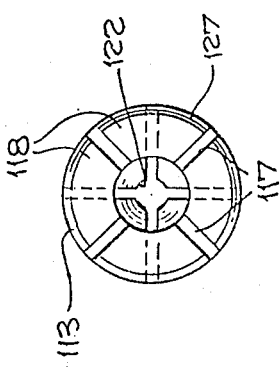
FIG. 16 is a longitudinal sectional view of one of the bushings.

The collett is provided at the right end as viewed in FIGS. 12 and 14 with a set of slots 117 forming a set of resilient fingers 118. The fingers encompass and form at the right end a lead receiving recess 119.

At the left end is a comparable set of slots 120 providing corresponding resilient fingers 121. The fingers 121 encompass and provide a lead receiving recess 122 relatively smaller than the first described lead receiving recess 119.

The collett 113 is adapted to be snuggly but slideably received in the mid portion 11 of the axial passageway 106 within the housing 104.

Cooperating with the set of fingers 118 at the right-hand end as viewed in FIG. 12 there is provided a bushing 123 which has extending through it a wrench pocket 124. There is a substantially flat exterior face 125 on the bushing and at the interior end is a flared recess 126 adapted to receive bevels 127 at the outside edges of the fingers 118. On the bushing are external threads 128 adapted to engage complementary internal threads 110 of the port 109. The same bushing 123 can merely be reversed in its orientation and used with the interal threads 108 of the port 107. At the left end the flared recess 126 is adapted to cooperate with bevels 130 on the outside edges of the fingers 121.

In operation when the lead 114 is one having a wire core 115 of relatively smaller diameter the wire core is inserted from the left end of the housing 104 as viewed in FIG. 12. This assumes prior to having been inserted that the two bushings 123 at the opposite ends have been threadably rotated outwardly toward the respective ends so that no pressure at that time is being applied to either the fingers 118 at the right-hand end or the fingers 121 at the left-hand end. As a consequence the fingers will be relaxed and expanded to their outermost positions. This condition opens the lead receiving recess 122 at the left-hand end to a size larger in diameter than the wire core 115 which as a consequence can be freely inserted through the wrench pocket 124 into the lead receiving recess 122. The lead is pushed far enough in so that the conventional exterior insulation is urged snuggly against the left end of the housing 104.

With the lead held in place as described a hexagonal wrench 131 is inserted into the port 109 at the right-hand end of the housing thence through the right-hand wrench pocket 124 and then by rotating the wrench 131 the rignt-hand bushing is advanced from right to left along the axial passageway 106 until the flared recess 126 first presses against the bevel 127. Pressure as described at the same time shifts the collett 113 in a direction from right to left thereby forcing the bevel 130 of the fingers 121 against the flared recess 126 of the bushing 123 which is at the left-hand end of the housing 104. There is of course no need to shift the position of the bushing 123 of the left-hand end because the collett is permitted to move, moving against the left-hand bushing 123 while the right-hand bushing 123 is being forced inwardly by the threaded engagement.

As a consequence the left-hand fingers 121 are urged radially inwardly into engagement with the exterior of the wire core 115 thereby to fasten it securely in position.

Conversely, when a lead is to be used which has a wire core 115 of relatively larger diameter the lead is applied to the right-hand end of the housing 104, assuming again that the bushings 123 have been rotated threadedly outwardly so as to relieve pressure from the bevels at the ends of the fingers at both ends. As a consequence the lead receiving recess 119 at the right-hand end of the collett will be expanded to a size adapted to freely receive the wire core which is of larger diameter, pressed into position until the lead itself is snuggly in engagement with the right-hand end of the housing 104. Held in this position the wrench 131 is applied to the left end namely through the port 107 and into the wrench pocket 124 of the left-hand bushing 123. On this occasion when the left-hand bushing is rotated in a direction to advance it into the collett the corresponding flared recess 126 first engages the bevel 130 of the fingers 121 and, after shifting the fingers radially inwardly the collett 113 is again shifted axially, this time in a direction from left to right thereby to press the bevel 127 of the fingers 118 into the flared recess of the right-hand bushing 123. As a consequence the right-hand fingers 118 are deflected radially inwardly into engagement with the wire core of relatively larger diameter thereby to fasten it securely in position. It is always possible to apply adequate pressure to the fingers which must be shifted into engagement with the wire core because although the fingers at the opposite ends are being deflected radially inwardly at the same time there is a limit to the inward movement which occurs when the corresponding slots are closed after which, all of the pressure applied by threadedly advancing the corresponding bushing can be transferred to the opposite ends where the appropriate fingers are being forced into snug electrical and mechanical engagement with the corresponding wire core.

Clearly by reversing the action, namely rotating the bushing which is at the opposite end of the housing from the lead in a direction to withdraw it from the collett, the fingers are permitted to expand releasing their grip on the wire core which can then be readily removed.

Having described the invention, what is claimed as new in support of Letters Patent is as follows:

1. In a cardiac pacemaker having an electric operating mechanism encapsulated in a case and a bore having opposite ends extending to the exterior of the case, the combination of an electric lead connecting fixture comprising a sleeve adapted to be anchored in said bore intermediate the opposite ends and electrically connected to said operating mechanism, said sleeve having an axial recess with an open end and an end wall at the opposite end, a flared portion in the recess, an opening through the end wall with internal threads, a collet comprising a shank with a sliding fit in said recess, a flared portion on said collet complementary to said flared portion in the recess, and a pocket in said shank for reception of an electric lead, said flared portion of the collet and a portion of the shank having slots providing for relative gripping movement, a hole at the end of the shank adjacent said end wall of the recess having internal threads matching the internal threads of the opening in the sleeve, and a captive collet draw screw comprising a shaft with a head at one end, a free end of said shaft having external threads complementary to said internal threads of the sleeve and the collet and a nonthreaded portion between the head and the external threads longer than the length of the internal threads in said sleeve and of diameter less than the minor diameter of said internal threads whereby said screw is rotatably retained in said sleeve, said collet being releasable and removable for replacement with a collet having a pocket of different inside configuration for reception of an electric lead of corresponding different configuration.

2. An electric lead connecting fixture as in claim 1 wherein there is a tool connection in said head of the collet draw screw.

3. An electric lead connecting fixture as in claim 1 wherein there is a plug in the bore at the end adjacent the collet draw screw having a self-closing wrench access hole therethrough.

4. An electrical connecting fixture as in claim 3 wherein said collet draw screw has a shaft at one end and a head at the opposite end, said shaft having threads at the free end and a smooth exterior between the threads and the head of diameter smaller than the minor diameter of said threads, said equalizer sleeve having at the end opposite the open end an interiorly threaded passage complementary to the threads on the draw screw and shorter than the length of said smooth exterior of the shank, whereby said draw screw will remain rotatably attached to the equalizer sleeve.

5. In a cardiac pacemaker as in claim 4 a tool connection in the head of said draw screw facing outwardly of said bore.

6. In a cardiac pacemaker as in claim 5 the end of the bore adjacent the sleeve being open for reception of an electric lead and a plug in the opposite end having a self-closing tool hole extending through the plug in alignment with the tool connection of said draw screw.

7. In a cardiac pacemaker having an electric operating mechanism encapsulated in a case and a bore having opposite ends extending to the exterior of the case, the combination of an electric lead connecting fixture comprising a fixed sleeve adapted to be anchored in said bore intermediate the opposite ends and electrically connected to said operating mechanism, opposite ends of said fixed sleeve having substantially identical flared recesses, an equalizer sleeve having an open end, a flared portion in said equalizer sleeve complementary to said flared recesses and at the end opposite said open end, a collet draw screw rotatably mounted in said equalizer sleeve, a split collet of selected outside diameter slidably contained in the fixed sleeve, said collet having a flared portion complementary to said flared recesses, an open end and an opposite interiorly threaded end, the threads on the draw screw being in threaded engagement with the threaded end of the collet, said equalizer sleeve being reversible end for end of the fixed sleeve for engagement with a collet of the same outside diameter but selected inside diameter on the side of the fixed sleeve opposite the equalizer sleeve.

8. A cardiac pacemaker unit comprising an electric operating mechanism encapsulated in a case and a bore having opposite ends extending to the exterior of the case, an electric lead connecting fixture comprising a sleeve anchored in said bore and electrically connected to said operating mechanism, said sleeve having an axial recess with an open end, a flared portion in the recess, an opening through the sleeve with internal threads, a collet comprising a shank with a sliding fit in said recess, a flared portion on said collet complementary to said flared portion in the recess, and a pocket in said shank for reception of an electric lead, said flared portion of the collet and a portion of the shank having slots providing for relative gripping movement, means forming a hole at the end of the shank having internal threads matching the internal threads of the opening in the sleeve, and a captive collet draw screw comprising a shaft with a head at one end, said collet being releasable and removable for replacement with a collet having a pocket of different inside configuration for reception of an electric lead of corresponding different configuration.

9. An electric lead connection for a cardiac pacemaker unit comprising a housing having an axial passageway therethrough providing opposite open ports each having internal threads,
a collet in said passageway,
a bushing for each port having external threads in engagement with the respective internal threads,
each said bushing having an axial wrench pocket extending therethrough and being movable into and out of engagement with the collet by wrench action,
said collet having a lead receiving bore extending therethrough providing a lead receiving opening at each end of the collet,
said collet having slots therein forming a plurality of spring fingers,
and finger depressing means respectively on the collet and the bushings enabling engagement of the collet with a lead inserted from either end by movement of the bushing at the opposite end.

10. An electric lead connection as in claim 9 wherein said collet has slots at each end forming a set of fingers at each end.

11. An electric lead connection as in claim 10 wherein the fingers at one end form a lead receiving recess of size different from a lead receiving recess formed by the fingers at the opposite end.

12. An electric lead connection as in claim 10 wherein there is a bevel on the exterior of the fingers at each end and a flared recess in each bushing receptive of the bevel of the respective fingers for deflecting the fingers radially inwardly to a lead gripping position.

13. An electric lead connection as in claim 9 wherein the midportion of the axial passageway in the housing is smooth and of diameter less than the root diameter of the external threads and the collet has a smooth cylindrical exterior in smooth sliding relationship with said midportion.

* * * * *